United States Patent
Laba et al.

(10) Patent No.: US 8,506,974 B2
(45) Date of Patent: *Aug. 13, 2013

(54) SILICON-FREE HYDROCARBONS PROVIDING AESTHETIC VOLATILITY

(75) Inventors: Dennis Laba, Langhorne, PA (US); Marie Yednak-Carpenter, Jackson, NJ (US); Priti Shah, Piscataway, NJ (US); Steven Cochran, Princeton, NJ (US)

(73) Assignee: Presperse Corporation, Somerset, NJ (US)

(*) Notice: Subject to any disclaimer, the term of this patent is extended or adjusted under 35 U.S.C. 154(b) by 963 days.

This patent is subject to a terminal disclaimer.

(21) Appl. No.: 12/269,608

(22) Filed: Nov. 12, 2008

(65) Prior Publication Data

US 2009/0123398 A1 May 14, 2009

Related U.S. Application Data

(60) Provisional application No. 60/987,510, filed on Nov. 13, 2007.

(51) Int. Cl.
| | |
|---|---|
| *A61K 8/02* | (2006.01) |
| *A61K 9/00* | (2006.01) |
| *A61K 8/00* | (2006.01) |
| *A61K 8/18* | (2006.01) |
| *A61Q 17/04* | (2006.01) |
| *A61Q 5/08* | (2006.01) |
| *A61Q 19/02* | (2006.01) |
| *A61Q 1/02* | (2006.01) |
| *A61Q 1/12* | (2006.01) |
| *A61Q 19/04* | (2006.01) |
| *A61Q 1/04* | (2006.01) |
| *A61Q 1/06* | (2006.01) |
| *A61Q 15/00* | (2006.01) |
| *A61Q 1/00* | (2006.01) |

(52) U.S. Cl.
USPC ............ 424/401; 424/400; 424/59; 424/62; 424/63; 424/64; 424/65; 424/69

(58) Field of Classification Search
None
See application file for complete search history.

(56) References Cited

U.S. PATENT DOCUMENTS

| | | | |
|---|---|---|---|
| 3,439,088 A * | 4/1969 | Edman | 424/63 |
| 5,534,246 A | 7/1996 | Herb | |
| 5,824,323 A * | 10/1998 | Fishman | 424/401 |
| 6,352,688 B1 * | 3/2002 | Scavone et al. | 424/65 |
| 2004/0247552 A1 * | 12/2004 | Blin et al. | 424/70.13 |
| 2006/0194932 A1 | 8/2006 | Farcet | |
| 2007/0166255 A1 | 7/2007 | Gupta | |
| 2007/0224140 A1 * | 9/2007 | Quadir et al. | 424/63 |

OTHER PUBLICATIONS

International Search Report and Written Opinion for International Application PCT/US2008/83244, Jan. 14, 2009 (Form PCT/ISA/220/210/237).
International Preliminary Report on Patentability and Written Opinion for corresponding PCT application No. PCT/US2008/083244, May 10, 2010. (PCT/IB/326/373/ISA/237).

* cited by examiner

Primary Examiner — Isis Ghali
(74) Attorney, Agent, or Firm — Timothy X. Gibson, Esq.; Gibson & Dernier LLP

(57) ABSTRACT

Non-silicone-based compositions including hydrocarbons of widely different structures and origins are combined into single, stable, homogenous products with both aesthetic and volatility properties similar to a cyclopentasiloxane. The combinations are useful to cosmetic formulators as full or partial replacement products for cyclopentasiloxanes, or "volatile silicones."

13 Claims, 1 Drawing Sheet

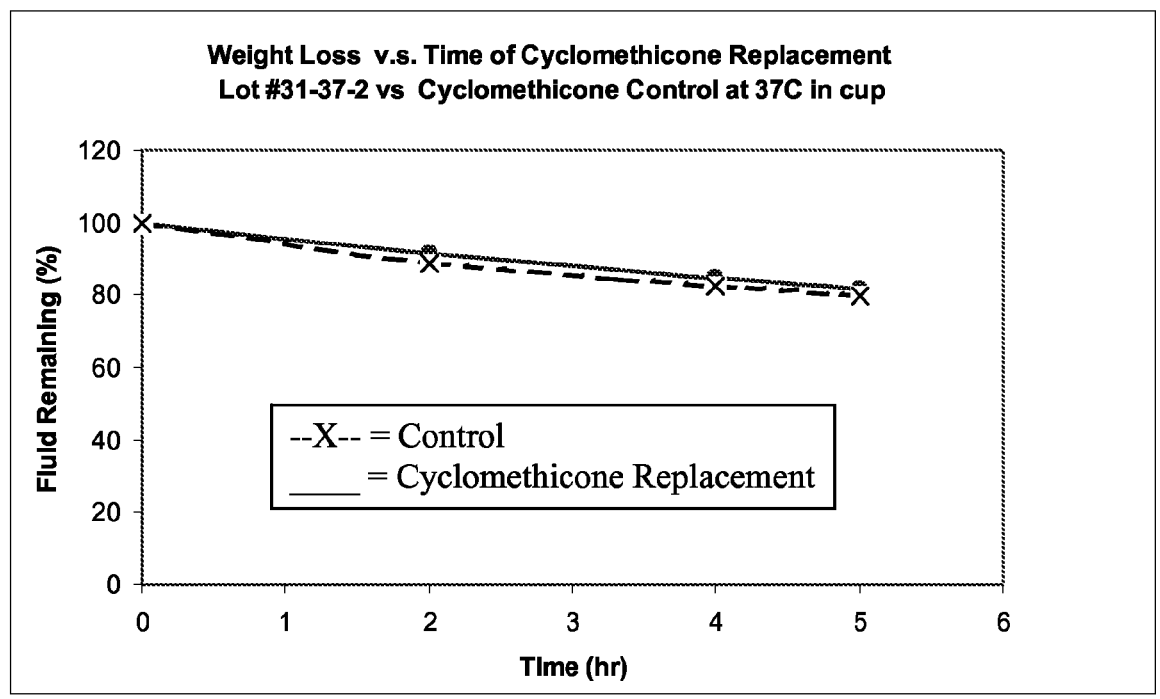

SILICON-FREE HYDROCARBONS PROVIDING AESTHETIC VOLATILITY

CROSS-REFERENCE TO RELATED APPLICATIONS

This application claims the benefit of U.S. Provisional Patent Application Ser. No. 60/987,510 filed Nov. 13, 2007, the entirety of which is incorporated herein by reference.

FIELD OF THE INVENTION

The present invention relates to silicone-free materials having aesthetic and volatility properties similar to cyclopentasiloxanes.

BACKGROUND OF THE INVENTION

Cosmetic formulating techniques have grown over the years due to a large variety and number of new raw material introductions. One of the changes over the last 25 years is the widespread use of cyclosiloxanes. These cyclic silicones have a number of properties that make them well suited for cosmetic formulating, including their volatility and aesthetic application properties. All varieties of cosmetic and personal care products have utilized these cyclic silicones to their advantage, such as creams and lotions, color cosmetics, hair care products and antiperspirants.

Recently, there have been safety concerns over cyclotetrasiloxanes (also called D4, or octamethylcyclotetrasiloxane) resulting in the removal of that chemical from most, if not all, formulations. Cyclopentasiloxane (also called D5 or decamethylcyclopentasiloxane) subsequently replaced D4 in formulations. Examples of D5 products include Dow Corning's DC 245 Fluid, and GE's SF 1202.

The structures of D4 and D5 are very similar, but the volatility rate of the D5 is not as high as the D4. Currently, the D5 is now also coming under scrutiny, and many formulators are being proactive and looking for a substitute product now, such as a silicone-free product, in the event D5 is to be removed from formulations.

Purified hydrocarbons, such as Isododecane (Permethyl® 99A) have been tried, but do not exhibit the same aesthetic properties as do the volatile silicones. Some companies have tried combinations of hydrocarbons to achieve a suitable volatility, but when the desired volatility is reached, these products still do not exhibit the required aesthetics, i.e., the feel on the skin, during application.

SUMMARY OF THE INVENTION

The current invention overcomes the problems of the prior art by combining multiple hydrocarbons of widely different structures and origins, into a stable, homogenous product with both aesthetic and volatility properties strikingly similar to a cyclopentasiloxane. Compounds in accordance with the present invention are useful to the cosmetic formulator as a full or partial replacement product for the questionable volatile silicone, both immediately during application, and after "dry down." The inventive compounds also fulfill the important requirement concerning a reasonable cost range, somewhat similar to the volatile silicones themselves.

OBJECTS OF THE INVENTION

It is an objective of this invention to provide to the cosmetic industry, as well as other industries that use volatile silicone compounds, a suitable raw material that can be used as a substitute for cyclopentasiloxane.

It is a further objective that the new materials have a similar volatility rate in use as the target and also display comparable aesthetics to the original volatile silicone when used in cosmetics. Still further objectives are to keep these new products "silicone-free," and prepared with materials that are priced similarly to the cyclopentasiloxanes, so substitution should not be restricted by price concerns.

In one embodiment a non-silicone-based composition which approximates the volatility and aesthetics of cyclomethicone is provided which includes at least two volatile hydrocarbon components and at least one nonvolatile hydrocarbon component.

In accordance with another embodiment non-silicone-based composition is provided having a first volatile hydrocarbon component selected from a C12-C14 hydrocarbon and a second volatile hydrocarbon component selected from a C13-C16 hydrocarbon and a nonvolatile hydrocarbon component. The volatile hydrocarbon components may be one or more straight or branched chain hydrocarbons, one or more isoparaffins such as a C12 to C14 isoparaffin or isododecane.

The nonvolatile hydrocarbon component may include a C13 to C21 hydrocarbon, and may be a mixture of isoalkanes and mixed structure hydrocarbons selected from linear, branched and cyclohydrocarbons. In one embodiment the nonvolatile hydrocarbon component is a C13 to C16 alkane or a C13 to C16 isoparaffin.

In another embodiment, the nonvolatile hydrocarbon may be selected from a C13 to C21 straight or branched chain alkyl ester of straight or branched chain carboxylic acid having 13 to 21 carbon atoms, and mineral oil.

In accordance with a preferred embodiment the present invention is a non-silicone-based composition which approximates the volatility and aesthetics of cyclomethicone having about 35% C12-C14 isoparaffin, about 55% C13-C16 isoparaffin, and about 10% C13-C15 alkane.

Compositions of the present invention are used as complete or partial substitute components for cyclopentasiloxanes in formulations including cosmetics, hair care products, skin care products, sun care products such as sunblock, antiperspirants, deodorants, tanning lotions, pharmaceutical creams and the like.

BRIEF DESCRIPTION OF THE DRAWINGS

FIG. 1 is a graphical depiction of a comparative evaporation rate (in cup) in accordance with one aspect of the present invention.

DETAILED DESCRIPTION OF THE PREFERRED EMBODIMENTS

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to "one embodiment" or "an embodiment" means that a particular feature, structure or characteristic described in connection with the embodiment is included in at least one embodiment of the invention. The appearances of the phrase "in one embodiment" in various places in the specification are not necessarily all referring to the same embodiment. The present invention in one aspect concerns compositions suitable for use as a replacement for cyclopentasiloxane, or volatile silicone, in a variety of products. Based on the testing described herein, in one embodiment the invention comprises three distinct components. The first two components are used to provide a level of volatility that approximates the cyclosiloxane, while being silicone-free. A third component, though not necessarily volatile by itself, when used in combination with the other two components provides the aesthetic properties needed for a volatile silicone replacement, yet demonstrates an unexpected level of volatility when tested in a thin film environment.

In an embodiment, the first two components used to provide the approximate volatility are both isoalkanes, but with different chain lengths. The shorter chains range from C12-14, and the longer ones from C13-16. The longer chain length material ranges in use concentration from between 20 and 80% by weight, preferably close to 60% and the shorter chain length hydrocarbon components are used at a range from 20 to 80% by weight, preferably close to 30%.

The third component of the composition may be selected from a mixed alkane with chains of different chemistries ranging from C13-21 or cosmetically acceptable oils. In an embodiment wherein the third component is a mixed alkane with chains of different chemistries ranging from C13-21, it is preferable that the mixed alkane is used at concentrations from 5-20%, preferably close to 10%. Chemical structures in this material may include isoalkanes, straight chained alkanes, and cycloalkanes. Cosmetically acceptable oils include but are not limited to isopropyl myristate, isopropyl palmitate, mineral oil, isononyl isononanoate, polybutenes, polyisobutenes and hydrogenated polyisobutenes.

In accordance with at least one preferred embodiment the invention includes:
C12-14 Isoparaffin at 35%
C13-16 Isoparaffin at 55%
and C13-15 Alkane at 10%.

The properties of volatile silicones that have made them successful in the cosmetic market over the years are based on the combination of volatility and aesthetics. Potential candidates for substitutes have generally fallen into three classes: Alcohols, hydrocarbons and synthetics. Volatile synthetic materials such as the fluorinated compounds, due to the manufacturing procedures, tend to be prohibitively expensive as a replacement for a material that is used at high levels for inexpensive mass market products. Alcohols (methanol, ethanol and isopropanol), while reasonably priced, evaporate quickly, but provide no suitably elegant feel, and leave an unacceptable cooling sensation on the skin caused by their low enthalpy of vaporization.

Hydrocarbons encompass a wide variety of chemical structures and therefore, a variety of different properties. Some commercial hydrocarbons are derived directly from fractionated petroleum, while others are built synthetically from very pure building blocks of a carefully produced specific fraction such as polyisobutenes. Within these groupings the most widely used family of hydrocarbons is the alkanes. Alkanes are fully saturated hydrocarbons that can exist in straight-chained structures (n-alkanes), branched structures (isoalkanes) and cyclic structures (cycloalkanes.) The alkanes show excellent stability due to the absence of carbon-carbon double bonds. Within these groups, the isoalkanes are widely used by cosmetic formulators and are exemplified by the line of Permethyl® Hydrocarbons from Presperse LLC (manufactured by INEOS) and the Isopars® isoalkanes from ExxonMobil. These materials come in a range of carbon chain-lengths, with the smallest chains showing volatility, with increasingly less volatility as they increase in length. Taken alone, or in combination, a suitable substitute to volatile silicones has not been found in the hydrocarbons, until the present invention. Though the volatility rate has been matched by combining isoalkanes, as shown below, the aesthetic properties were still not suitable. Non-volatile, or longer chain length alkanes start to approach some of the aesthetic properties, but lack in their volatility. Whereas isododecane (C12) is widely employed for its volatility, isohexadecane (C16) is significantly less volatile, and is more widely employed for its nonvolatile property. In comparison to isododecane, isohexadecane is considered by the industry as only "slightly volatile" or "substantially non-volatile." In fact, some longer chain alkanes are used specifically in cosmetics for their lack of volatility, and are widely used for the long-lasting emollient properties in creams and lotions, long-wearing properties in lipsticks and waterproofing properties in sunscreens. They have not been traditionally thought of as "volatile" products, nor part of a replacement strategy for volatile materials.

Another branch of hydrocarbons are represented by "mixed" alkanes and exemplified by the line of Gemseal® from Total Petrochemicals, products ranging from C13-15 alkanes to C18-21 alkanes. These materials, unlike the isoparaffins, contain various amounts of cycloalkanes and n-alkanes as well as the branched chained isoparaffins. Because of their mixed chemistries, they demonstrate different aesthetic properties than the pure isoalkanes. They are typically promoted as "non-volatile" hydrocarbons that produce emolliency, water-proofing and long-wear effects. In fact a case is usually made about their lack of volatility or vapor pressure, as they are exempt from current VOC regulations in California.

Chemicals other than these described are used in the cosmetic industry for their emollient properties. Esters, such as isopropyl myristate, isopropyl palmitate, alkyl benzoates, octyl palmitate and others have all been used, but are all non-volatile products used for their emolliency, non-volatile properties, or contributions to the overall feel of the cosmetic formulation.

In looking for a full replacement product for cyclopentasiloxane, approximating the volatility is necessary. Panel tests were performed wherein a products were evaluated according to the following scale:

| SCORE | SLIP | PERCEIVED VOLATILITY | RESIDUE/ GREASINESS |
|---|---|---|---|
| 1 | No Slip- No feeling of Lubrication or draggness on skin | Non-volatile | Similar to Cyclomethicone (Absorbs quickly and no film formation left on skin and) |
| 2 | Similar to Cyclomethicone (Offers slight slip) | Slight volatility | Slight residue/greasiness provides light and silky afterfeel |
| 3 | Moderate Slip | Moderate volatility | Moderate residue/greasiness |
| 4 | Medium to High Slip | Similar to Cyclomethicone (Medium to High Volatility-dries quickly on skin) | Medium to High residue/greasiness |

-continued

| SCORE | SLIP | PERCEIVED VOLATILITY | RESIDUE/ GREASINESS |
|---|---|---|---|
| 5 | High Slip, very Lubricous imparts drag without friction | High volatility - Ability to absorb readily upon application (Dries immediately on skin) | High residue/greasiness (Unable to absorb and rub in quickly, provides film formation on skin) |

The scale was pre-defined to allow subjective assessment to be categorized into levels. It will be apparent to those skilled in the art the scale is typical of those used for a subjective panel test. The criteria for subjective volatility is how fast the sample evaporates off from skin, or it's ability to absorb or evaporate readily upon application. The criteria for subjective level of residue/greasiness is how much material is still left on the skin or it's inability to absorb or rub in quickly.

Table 1 shows the results of a number of panel tests done on individual isoparaffins and their combinations.

TABLE 1

(scale 1-5, with 5 being the highest level)

| MATERIALS | SLIP | PERCEIVED VOLATILITY | RESIDUE/ GREASINESS |
|---|---|---|---|
| Control (cyclomethicone) | 2 | 4 | 1 |
| C12-14 Isoparaffins | 1 | 5 | 1 |
| C13-16 Isoparaffins | 3 | 2 | 2 |
| Isododecane | 1 | 5 | 1 |
| Isohexadecane | 3 | 2 | 2 |
| C12-14 Isoparaffin/C13-16 Isoparaffin, 50:50 ratio | 2 | 3 | 2 |
| C12-14 Isoparaffin/C13-16 Isoparaffin, 60:40 ratio | 1 | 4.5 | 1 |
| C12-14 Isoparaffin/C13-16 Isoparaffin, 40:60 ratio | 1 | 4.5 | 1 |

It can be seen that the combination of C12-14 Isoparaffin and C13-16 Isoparaffin approximates the volatility of the D5 or cyclomethicone, but still lacks the slip and comparable afterfeel needed. Other combinations of hydrocarbons were not adequately volatile, and lacked the proper aesthetics.

Table 2 shows the results when a third ingredient was added to the mixture, to try to improve the slip and temporary emolliency or afterfeel shown with the cyclopentasiloxanes:

TABLE 2

(scale 1-5, with 5 being the highest level)

| MATERIALS | SLIP | PERCEIVED VOLATILITY | RESIDUE/ GREASINESS |
|---|---|---|---|
| C12-14 Isoparaffin/C13-16 Isoparaffin/C13-15 Alkanes, 35:60:5 ratio | 2 | 4.5 | 1 |

The amount of the C13-15 alkane was kept low initially, as it was expected that the addition of any significant amount of such a non-volatile material to a volatile silicone replacement product, would necessarily overshadow the long-term aesthetics, thereby rendering the product unacceptable. Surprisingly, the addition of C13-15 alkane moved the replacement product more towards the desired effect. When tested on the skin, it unexpectedly retained the proper volatility and yet at the same time, provided a slip or emolliency better than the previous attempts without the C13-15 alkane. Increasing the amount of C13-15 alkane, as in Table 3, showed that above a certain amount, the final product started to exhibit some of the negative attributes of greasiness or less perceived volatility. Though any of the Gemseal® line of mixed alkanes work to a certain degree, the C13-15 alkanes are preferred, based on application aesthetics and dry down characteristics.

TABLE 3

| MATERIALS | SLIP | PERCEIVED VOLATILITY | RESIDUE/ GREASINESS |
|---|---|---|---|
| C12-14 Isoparaffin/C13-16 Isoparaffin/C13-15 Alkanes, 35:55:10 ratio | 1 | 4 | 1 |
| C12-14 Isoparaffin/C13-16 Isoparaffin/C13-15 Alkanes, 30:55:15 ratio | 1 | 3.5 | 2 |
| Polyisobutene | 1.5 | 3.5 | 1 |
| Hydrogenated Polyisobutene | 0 | 4 | 0 |
| Polybutene | 3 | 3 | 1 |

Without being restricted to any single theory, it is thought that the aesthetic feel coming from the addition of the mixed alkanes is due to the variety of structures available in these products, containing not only the isoparaffins, but also a level of straight chained alkanes and cycloalkanes. This chemistry is in direct contrast to the isoalkanes, where only one chemical structure of hydrocarbons is available. The mixed structures together with the isoparaffins produce a thicker, more cushioned feel when the combination is rubbed on the skin, providing a cyclomethicone-like sensation.

In other embodiments, an additional ingredient may be selected from cosmetically acceptable oils, such as but not limited to those in Table 4. Exemplary compositions in accordance with Table 4 may be considered to have suitable properties by some cosmetic formulators with particular needs. As in the previous case, the inclusion of a totally non-volatile material to help match properties of a fully volatile material was unexpected and is considered novel.

TABLE 4

Materials tested at 10% level with C12-14 Isoparaffin/C13-16 Isoparaffin/C13-15 Alkanes, 35:55 parts
(scale 1-5, with 5 being the highest level)

| INGREDIENT TESTED | SLIP | PERCEIVED VOLATILITY | RESIDUE/ GREASINESS |
|---|---|---|---|
| Isopropyl Myristate | 2 | 3 | 1 |
| Isopropyl Palmitate | 2 | 3 | 1 |
| Mineral Oil | 3 | 2.5 | 2 |
| Isononyl Isononanoate | 2 | 3.5 | 1 |
| Polyisobutene | 1.5 | 3.5 | 1 |
| Hydrogenated Polyisobutene | 0 | 4 | 0 |
| Polybutene | 3 | 3 | 1 |

The suitability for use of replacement materials for cyclomethicones in cosmetics is very dependent on the perception of the aesthetics of the finished product. As subjective perception is not always directly related to laboratory testing results, it becomes more important to match the perceived aesthetics than it is to exactly match the tested physical properties. If physical properties match perfectly, but the aesthetics are off, the product would be useless as a replacement in the cosmetic industry. However, if the aesthetic properties match, and the physical properties are slightly off, the product could still be used successfully by someone skilled in the cosmetic formulating arts. This distinction is important, as the inventors were surprised to see that though the aesthetics of the preferred invention closely matched cyclopentasiloxane, the tested physical properties did vary.

In studying volatility, a certain weight of each product was placed in weighing boats, and the evaporation rates were tracked gravimetrically over time. Upon being faced with a known non-volatile actually contributing to the perceived feel of matched volatility, the present inventors rethought their test methods. Since consumer use of creams, lotions, hair products and color cosmetics is based on the volatility taking place in thin films and at 37 degrees C., such as is created when rubbed onto the skin, the inventors retested the materials at 37 degrees C. and also by using a "bird applicator" to draw down a thin film of the liquid on a piece of glass, and were surprised to find that the volatility characteristics changed dramatically. The differences found showed that the combination material did volatilize completely, in spite of the seemingly non-volatile components. The results are shown in FIG. 1 and in Table 5.

TABLE 5

| MATERIALS TESTED | | RELATIVE VOLATITY IN CUP AT 37 C. | RELATIVE VOLATILITY ON GLASS PLATES |
|---|---|---|---|
| Control | Cyclomethicone (control) | Approx. 80% remaining after 5 hours | Completely volatile in 1 hour |
| Cyclomethicone Replacement Lot # 31-37-3 (SiClone ™ SR-5) | C12-14 Isoparaffin/ C13-16 Isoparaffin/ C13-15 Alkanes, 35:55:10 ratio | Very Similar to control | Completely volatile in 1 hour |

EXAMPLES

The following examples demonstrate certain aspects of the present invention. However, it is to be understood that these examples are for illustrative purposes only and do not purport to be wholly definitive as to conditions and scope of this invention. For example, it will be apparent to those skilled in the art, that even a partial replacement of volatile silicone with the current invention may be advantageous under certain conditions.

A further understanding of the invention may be obtained from the following nonlimiting examples. While not every possible formulation is exemplified herein, it will be understood to those skilled in the art that the compositions herein can be used as complete or partial substitute components for cyclopentasiloxanes in formulations including cosmetics, hair care products, skin care products, sun care products such as sunblock, antiperspirants, deodorants, tanning lotions, pharmaceutical creams and the like. Suitable cosmetically and pharmaceutically acceptable carriers are known to those skilled in the art.

Example 1

The following cream product with the embodiment EXP-SR5, now SiClone™ SR-5 from Presperse LLC and listed below, was produced and tested against a control product using DC 245 Fluid, a volatile silicone product from Dow Corning, and found to be indistinguishable in blind triangle tests.
EXP-SR5 (SiClone™ SR-5) Composition
    C12-14 Isoparaffins 35%
    C13-16 Isoparaffins 55%
    C13-15 Alkanes 10%

| | Test Material, % | Control, % |
|---|---|---|
| PHASE A | | |
| EXP-SR5 (SiClone ™ SR-5) (Cyclomethicone Replacement) | 10 | |
| Dow 245 (Cyclomethicone) | | 10 |
| Phoenomulse-100 (emulsifier) Polyhydroxystearic acid/Isononyl Isononanoate/Ethylhexyl Isononanoate/Sodium Cocamidopropyl PG-Dimonium Chloride Phosphate | 15 | 15 |
| PHASE B | | |
| DEIONIZED WATER | 67.5 | 67.5 |
| ZILGEL V V (Bodying agent) Glycerin/water/sodium polyacrylate | 5 | 5 |
| PHASE C | | |
| Sepigel N.S. (Thickener) Hydroxyethyl acrylate/ sodium acryloyldimethyl taurate copolymer & squalane & polysorbate 60 | 2.5 | 2.5 |

Procedure:—

Mix phase A at high shear for 10 seconds

Blend phase B until uniform, then combine phases A and B with slow propeller mixing until uniform.

Add Phase C to phase AB with medium mixing until uniform.

Example 2

The following color cosmetic foundation was produced and tested against a control product using DC 245 Fluid in place of the EXP-SR5 (SiClone™ SR-5), and found to be indistinguishable in blind triangle tests.

| TRADE NAME | INCI NAME | SUPPLIER | % W/W |
|---|---|---|---|
| PHASE A | | | |
| Oleosperse Yellow Iron Oxide | Yellow Iron Oxide (and) Dimethicone | Presperse LLC | 2.00 |
| Oleosperse Red Iron Oxide | Red Iron Oxide (and) Dimethicone | Presperse LLC | 0.85 |
| Olesoperse Black Iron Oxide | Black Iron Oxide (and) Dimethicone | Presperse LLC | 0.25 |
| Oleosperse Titanium Dioxide | Titanium Dioxide (and) Dimethicone | Presperse LLC | 8.00 |
| Spheron L-1500 | Silica | Presperse LLC | 3.00 |
| Sericite PHN | Mica | Presperse LLC | 1.00 |
| PHASE B | | | |
| EXP-SR5 (SiClone ™ SR-5) | C13-16 Isoparaffin (and) C12-14 Isoparaffin (and) C13-C15 Alkane | Presperse LLC | 30.00 |
| DC Formulation Aid 5200 | Lauryl PEG/PPG-19/18 Methicone | Dow Corning | 2.00 |
| Abil EM-90 | Cetyl PEG/PPG-10/1 Dimethicone | Degussa | 1.00 |
| Versagel MD-1600 | Isododecane (and) Ethylene Propylene/ Styrene (and) Butylene/Ethylene/ Styrene Copolymer | Penerco | 8.00 |
| PHASE C | | | |
| Deionzied Water | Water | N/A | 41.40 |
| Sodium Chloride | Sodium Chloride | N/A | 0.75 |
| Phoenotine C-35 | Sodium Cocamidopropyl PG-Dimonium Chloride Phosphate | Phoenix Chemical | 0.75 |

-continued

| TRADE NAME | INCI NAME | SUPPLIER | % W/W |
|---|---|---|---|
| Euxyl PE 9010 | Phenoxyethanol (and) Ethylhexylglycerin | Schulke | 1.00 |

Procedure:

Combine Phase A in the order listed (combine only 80% of the pigments, use the remaining 20% to adjust the color-shade to standard) and pass through the pulverizer twice. Drawdown powder phase and check for streaking If needed, re-pulverize until color is evenly dispersed. Add Phase A to Phase B with homogenization. Homogenize until uniform. Premix Phase C in order of addition of materials. Once Phase C is uniform, very slowly add to Phase AB with homogenization. Homogenize until uniform. Increase speed for uniformly and viscosity as needed.

Example 3

The following Hair Serum with EXP-SR5 (SiClone™ SR-5) was produced and tested against a control product using DC 245 Fluid, and found to be indistinguishable in blind triangle tests.

| TRADE NAME | INCI NAME | SUPPLIER | % W/W |
|---|---|---|---|
| EXP-SR-5 (SiClone™ SR-5) | C13-16 Isoparaffins (and) C12-14 isoparaffin (and) C13-C15 Alkane | Presperse LLC | 46.00 |
| Siltech S-708 | Dimethiconol | Siltech Corp. | 45.00 |
| Escalol 557 | EthylHexylMethoxyCinnamate | ISP Corp. | 4.50 |
| Drakeol 7 | Mineral Oil | Penreco | 3.00 |
| INULA HC | Caprylic/Capric Triglyceride - Inula Crithmoïde Extract | Presperse LLC | 1.00 |
| Fragrance | Fragrance | | 0.50 |

Combine the ingredients under slow prop mixing, in the order listed. Allow batch to mix well before adding each ingredient. Continue adding and mixing until a clear liquid is achieved.

Example 4

The following antiperspirant stick formulation was produced and found to be indistinguishable from cyclomethicone-based antiperspirant sticks:

| TRADE NAME | INCI NAME | SUPPLIER | % W/W |
|---|---|---|---|
| PHASE A | | | |
| EXP-SR-5 (SiClone™ SR-5) | C13-C16 Isoparaffin (and) C12-C14 Isoparaffin (and) C13-C15 Alkane | Presperse LLC | 55.50 |
| PHASE B | | | |
| Stearyl Alcohol | Stearyl Alcohol | Croda | 20.00 |
| PHASE C | | | |
| Cutina HR | Hydrogenated Castor Oil | Cognis | 3.50 |
| Reach AZP-908 | Aluminum Zirconium Tetrachlorohydrex GLY | Reheis, Inc. | 20.00 |
| Micro Ace P-2 | Talc | Presperse LLC | 1.00 |

Procedure:

In an appropriate flask with a condenser, heat Phase A to 65° C. and Add Phase B with continuous mixing (medium speed, 60-65° C.). Allow Phase B to melt completely before proceeding to next step. Add Phase C in the order listed (medium speed, 60-65° C.). Allow each ingredient to fully disperse before proceeding to the next in order. Continue mixing until batch is homogeneous. Cool batch with mixing to 45-50° C. Fill components.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A non-silicone-based composition consisting essentially of:
   about 35% of a first hydrocarbon component selected from a C12-C14 isoparaffin, about 55% of a second hydrocarbon component selected from a C13-C16 isoparaffin, and about 10% of at least one further component selected from the group consisting of a $C_{13-15}$ mixed alkane and a cosmetically acceptable oil,
   wherein the composition approximates the volatility and aesthetics of cyclomethicone.

2. A non-silicone-based composition according to claim 1 consisting of:
   a. about 35% C12-C14 Isoparaffin,
   b. about 55% C13-C16 Isoparaffin, and
   c. about 10% C13-C15 Alkane.

3. A non-silicone-based composition which approximates the volatility and aesthetics of cyclomethicone comprising a component consisting essentially of:
   about 35% of a first hydrocarbon component selected from a C12-C14 isoparaffin, about 55% of a second hydrocarbon component selected from a C13-C16 isoparaffin and about 10% of a further component selected from the group consisting of a $C_{13-15}$ mixed alkane and a cosmetically acceptable oil,
   the non-silicone based composition further comprising a cosmetically or pharmaceutically acceptable carrier.

4. A non-silicone-based composition according to claim 3 wherein the component consists of
   about 35% C12-C14 Isoparaffin, about 55% C13-C16 Isoparaffin and about 10% C13-C15 Alkane.

5. A cosmetic formulation comprising the composition of claim 4.

6. A hair care formulation comprising the composition of claim 4.

7. A skin care formulation comprising the composition of claim 4.

8. A sun care formulation comprising the composition of claim 4.

9. A color cosmetic formulation comprising the composition of claim 4.

10. An antiperspirant formulation comprising the composition of claim 4.

11. A deodorant formulation comprising the composition of claim 4.

12. A tanning formulation comprising the composition of claim 4.

13. A pharmaceutical cream or lotion formulation comprising the composition of claim 4 and a pharmaceutically acceptable carrier.

* * * * *